Dec. 4, 1962 E. S. BOERNER Plant Pat. 2,200
ROSE PLANT
Filed Jan. 31, 1962
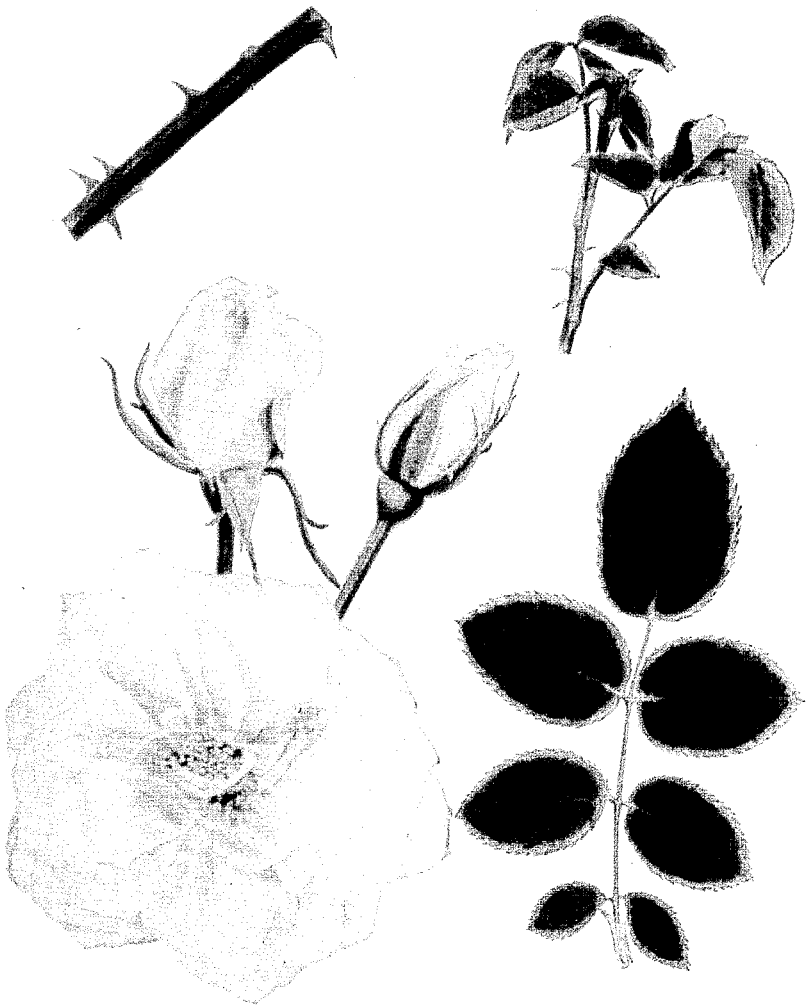
Inventor.
E. S. Boerner
By: Robb & Robb
Attorneys.

United States Patent Office

Plant Pat. 2,200
Patented Dec. 4, 1962

2,200
ROSE PLANT

Eugene S. Boerner, Newark, N.Y., assignor to Jackson & Perkins Company, Newark, N.Y., a corporation of New York Filed Jan. 31, 1962, Ser. No. 170,296
1 Claim. (Cl. 47—61)

The present invention relates to a new and distinct variety of rose plant of the hybrid tea class, which was originated by me by crossing an unnamed and unpatented Yellow Hybrid Tea seedling of unidentified parentage with the variety "Pageant" (Plant Patent No. 1252).

The primary objective of this breeding was to produce a new rose variety of the Hybrid Tea class which is characterized by bearing highly colored flowers, combined with good flower fragrance and great floriferousness. This objective was fully achieved, along with other desirable features, as evidenced by the following combination of characteristics which are outstanding in the new variety and which distinguish it from its parents, as well as from all other varieties of which I am aware:

(1) Great floriferousness;
(2) Large flower size;
(3) Long-lasting qualities of the flowers both on the bush and as cut flowers;
(4) Good Old Rose Perfume flowers fragrance; and
(5) A distinctive and attractive general color tonality of the flowers corresponding to Rose Doree, lightly overcast with Eosine Pink, which is a new color in the class of hybrid tea roses.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed Yellow Hybrid Tea seedling of unidentified parentage.
*Pollen parent.*—"Pageant".

Classification:
*Botanic.*—Hybrid tea.
*Commercial.*—Hybrid tea.

*Flower*

(Observations made from specimens grown outdoors at Newark, New York, about mid-morning during the early part of the month of September.)

Blooming habit: Recurrent—continuous; very floriferous.
Bud:
*Size.*—Large.
*Form.*—Pointed; is not affected by wet or hot weather.
*Color.*—When sepals first divide—Jasper Red, Plate 13. When petals begin to unfurl—Scarlet-Red, Plate 1, lightly overcast with Scarlet, Plate 1. When half-blown—inside of petals—Begonia Rose, Plate 1, very lightly overcast with Scarlet-Red, Plate 1. Reverse of petals—Scarlet, Plate 1, lightly overcast with Coral Red, Plate 13.

*Sepals.*—Slightly branched; curl back when petals begin to unfurl. Color—inside—Pale Tiber Green, Plate 18. Outside—Rinnemann's Green, Plate 18.
*Calyx.* — Color — Rinnemann's Green, Plate 18. Shape—apple. Size—broad. Aspect—smooth. Odor when rubbed—none.
*Peduncle.* — Length — Medium. Aspect — Rough. Strength — erect; heavy. Color — Calla Green, Plate 5.
*Opening.*—Opens up well; is not affected by adverse weather conditions.

Bloom:
*Size.*—Very large. Average size when fully expanded—5 inches to 5½ inches.
*Borne.*—Both singly and several together.
*Stems.*—Medium length; strong.
*Form when first open.*—Semi-cupped. Permanence—retains its form to the end.
*Petalage.*—Very double (many petals and stamens hidden). Number of petals under normal conditions—from 35 to 40.
*Color.*—Center of flower—Scarlet-Red, Plate 1, lightly overcast with Rose Doree, Plate 1. Outer petals—Eosine Pink, Plate 1, very lightly overcast with Rose Doree, Plate 1. Base of petals (aiglet)—Lemon Chrome, Plate 4. Inside of petals—Rose Doree, Plate 1, lightly overcast with Eosine Pink, Plate 1. Reverse of petals—Eosine Pink, Plate 1. General tonality from a distance—Rose Doree, Plate 1, lightly overcast with Eosine Pink, Plate 1.
*Discoloration.*—General tonality at end of first day—Rose Doree, Plate 1, lightly overcast with Eosine Pink, Plate 1. Second day—Rose Doree, Plate 1, lightly overcast with Eosine Pink, Plate 1. Third day—Eosine Pink, Plate 1, very lightly overcast with Rose Doree, Plate 1.

Petals:
*Texture*—Thick; is not affected by wet or hot weather.
*Appearance.*—Inside—satiny. Outside—shiny.
*Form.*—Oval.
*Arrangement.*—Imbricated (regularly ararnged shingle-like).
*Petaloids in center.*—Few; large.
*Persistence.*—Drop off cleanly.
*Fragrance.*—Moderate; very distinctive. Nature—Old Rose Perfume (Centifolia).
*Lasting quality.*—On the plant—very long. As cut flower—long.

*Genital Organs*

Stamens, anthers: Large; many; regularly arranged around styles. Color—Bittersweet Orange, Plate 2.
Stamens, filaments (threads): Long. Color—Scarlet, Plate 1.
Pollen: Color—Orient Pink, Plate 2.
Styles: Bunched; uneven length; medium length; thin.
Stigmas: Color—Ochraceous Salmon, Plate 15.
Ovaries: All enclosed in calyx.
Hips: None.
Seeds: None.

*Plant*

Form: Bush.
Growth: Vigorous; upright.
Foliage: Compound of 5–7 leaflets.
*Size.*—Medium.
*Quantity.*—Normal.

Color.—New foliage: Upper side—Absinthe Green, Plate 31, lightly overcast with Brick Red, Plate 13 on the outer edge of the petals. Under side—Pompeian Red, Plate 13, with midrib Chromium Green, Plate 32. Old foliage: Upper side—Forest Green, Plate 17. Under side—Light Bice Green, Plate 17.

*Shape.*—Oval pointed.

*Texture.* — Upper side — leathery. Under side — smooth.

*Ribs and veins.*—Prominent.

*Edge.*—Serrated (saw-toothed).

*Serration.*—Both double and single; small.

*Leaf stem.*—Color—Citrine, Plate 4. Under side—prickly.

*Stipules.*—Medium length; bearded.

Wood:

*New wood.*—Color—Biscay Green, Plate 17, lightly overcast with Isabella Color, Plate 30. Bark—smooth.

*Old wood.*—Color—Dark Cress Green, Plate 31. Bark—smooth.

Thorns:

*Thorns.*—Quantity: On main stalks from base—ordinary. On laterals from stalk — ordinary. Form—narrow base; medium length; hooked downward. Color (when young)—Coral Pink, Plate 13. Position—irregular.

*Prickles.*—Quantity—on main stalks — none. On laterals—none.

*Short needles.*—Quantity—On main stalks—none. On laterals—none.

I claim:

A new and distinct variety rose plant of the hybrid tea class, substantially as herein shown and described, characterized particularly as to novelty by the unique combination of great floriferousness, large flower size, long-lasting qualities of the flowers both on the bush and as cut flowers, a very distinctive Old Rose Perfume flower fragrance, and a distinctive and attractive general color tonality of the flowers corresponding to Rose Doree, lightly overcast with Eosine Pink.

No references cited.